US00PP35580P2

(12) United States Plant Patent
Townsend

(10) Patent No.: US PP35,580 P2
(45) Date of Patent: Jan. 16, 2024

(54) HOP PLANT NAMED 'IH13022'

(50) Latin Name: ***Humulus lupulus* L.**
Varietal Denomination: IH13022

(71) Applicant: Oregon State University, Corvallis, OR (US)

(72) Inventor: Michael Shaun Townsend, Corvallis, OR (US)

(73) Assignee: Indie Hops, LLC, Portland, OR (US)

( * ) Notice: Subject to any disclaimer, the term of this patent is extended or adjusted under 35 U.S.C. 154(b) by 0 days.

(21) Appl. No.: 18/090,334

(22) Filed: Dec. 28, 2022

(51) Int. Cl.
*A01H 5/00* (2018.01)
*A01H 6/28* (2018.01)

(52) U.S. Cl.
USPC ..... Plt./236
CPC ..... *A01H 6/28* (2018.05)

(58) Field of Classification Search
USPC ..... Plt./236
CPC ..... A01H 6/28; A01H 5/00
See application file for complete search history.

*Primary Examiner* — Keith O. Robinson
(74) *Attorney, Agent, or Firm* — Klarquist Sparkman, LLP

(57) ABSTRACT

A new and distinct hop plant cultivar named 'IH13022' is disclosed, characterized by its maturity date, tolerance to downy mildew, yield, essential oil content, alpha acid content, and beta acid content.

4 Drawing Sheets

Genus and species: *Humulus lupulus* L.
Variety denomination: 'IH13022'.

BACKGROUND

The present disclosure comprises a new and distinct cultivar of *Humulus lupulus* L., and hereinafter referred to by the cultivar name 'IH13022'.

The new hop plant resulted from open-pollinated seed collected from a 'Sorachi Ace' (unpatented) female plant in 2013. 'Sorachi Ace' was developed and released by Sapporo Breweries in Japan during the mid-1980s, and this cultivar has had very limited commercial success in the United States. The paternal parent is unknown. The resulting hop plant was selected when growing in a greenhouse in Corvallis, Oregon in February 2014.

SUMMARY

During September 2013, open-pollinated seed was collected from the female hop cultivar 'Sorachi Ace' near Corvallis, Oregon (FIG. 1). 'Sorachi Ace' is a publicly available hop cultivar developed and released by Sapporo Breweries in Japan during the mid-1980s. Seed was collected by hand, stratified for 8 weeks at 34° F., and planted into flats containing a standard soil mix in a greenhouse in January 2014. Established hop seedlings were evaluated for general vigor and powdery mildew (*Podosphaera macularis* [Wallr.] U. Braun & S. Takam) resistance, and 'IH13022' was one of the seedlings selected and transplanted into 1-gallon pots. Once established, potted plants were placed under a 6-foot short trellis system during June 2014 in a field nursery located near Corvallis, Oregon. Plants were evaluated for general vigor, sex, powdery and downy mildew (*Pseudoperonospora humuli* [Miyabe & Takah.] G. W. Wilson) resistance, and pest resistance during the summer of 2014. Selected plants were transplanted into a field evaluation nursery under a standard 18-foot trellis in January 2015. 'IH13022' was determined to be a female cultivar in 2015, and was evaluated for downy mildew resistance in 2015, 2016, and 2018, and powdery mildew resistance in 2015, 2017, and 2018. Due to inconsistent pest pressure, 'IH13022' was evaluated for hop aphid (*Phorodon humuli* Schrank) and hop looper (*Hypnea humuli* Harris) resistance only in 2017. Yield potential and preliminary sensory evaluations were determined in 2017 and 2018.

Based upon agronomic performance and the initial sensory assessment, 'IH13022' was propagated via rhizomes obtained from the individual motherplant in February 2018 with additional propagation from stem cuttings in a greenhouse in Corvallis, Oregon. Under the direction and control of the inventor, plants were established in 1-gallon pots and transplanted into replicated field nurseries in Oregon's Willamette Valley during the summer of 2018. These fields were managed using standard hop production techniques. Due to aggressive disease and pest control measures, only yield, chemistry, and sensory data were collected from these plots during the 2019, 2020, and 2021 growing seasons. Beginning in October 2019, 'IH13022' entered internal sensory evaluations utilizing dry rub and dry hop analyses.

The 'IH13022' hop variety is distinguished from other hop varieties due to the following unique combination of agronomic and chemical characteristics. When grown in Oregon's Willamette Valley, 'IH13022':

1. Matures later than 'OR91331' (U.S. Plant Pat. No. 31,042) and 'Sorachi Ace'
2. Is tolerant of downy mildew similar to 'Sorachi Ace' whereas 'OR91331' is resistant
3. Yields less than 'OR91331', but similar to 'Sorachi Ace'
4. Typically contains lower amounts of essential oil than 'OR91331' and 'Sorachi Ace'
5. Contains a lower alpha acid content than 'OR91331', but similar to 'Sorachi Ace'
6. Contains less beta acids than either 'OR91331' or 'Sorachi Ace'

7. Contains differing amounts of 20 essential oil components implicated in beer flavor and aroma as compared to 'OR91331' and 'Sorachi Ace'

Asexual reproduction of the new hop cultivar 'IH13022' was first performed in Corvallis, Oregon by rhizomes in 2018. Subsequent propagations have been via rhizomes and stem cuttings, and this cultivar has remained genetically stable.

DETAILED BOTANICAL DESCRIPTION

Figure 1:
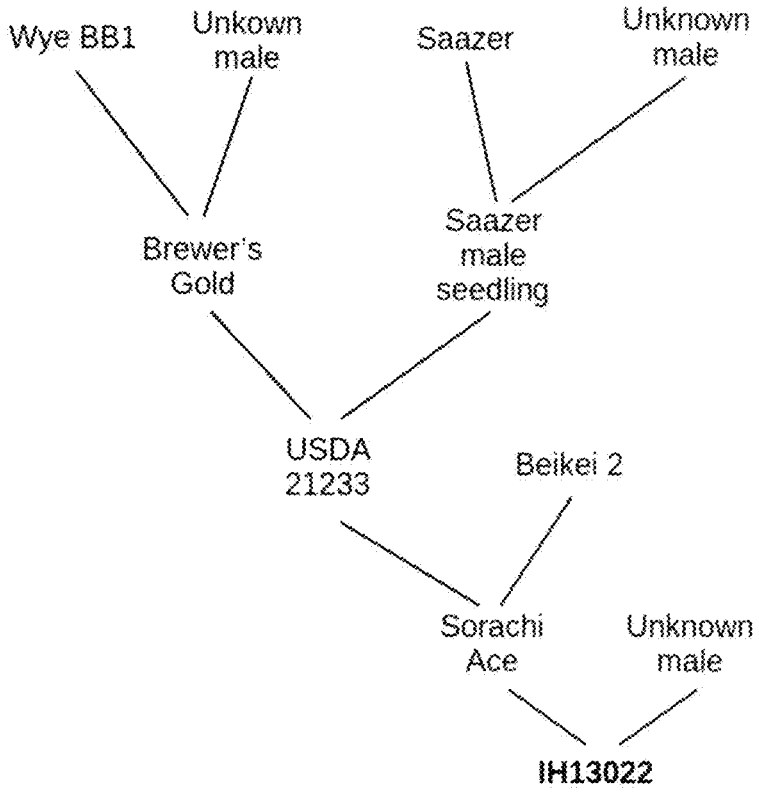
FIG. 1 illustrates the pedigree for 'IH13022'.
Figure 2:
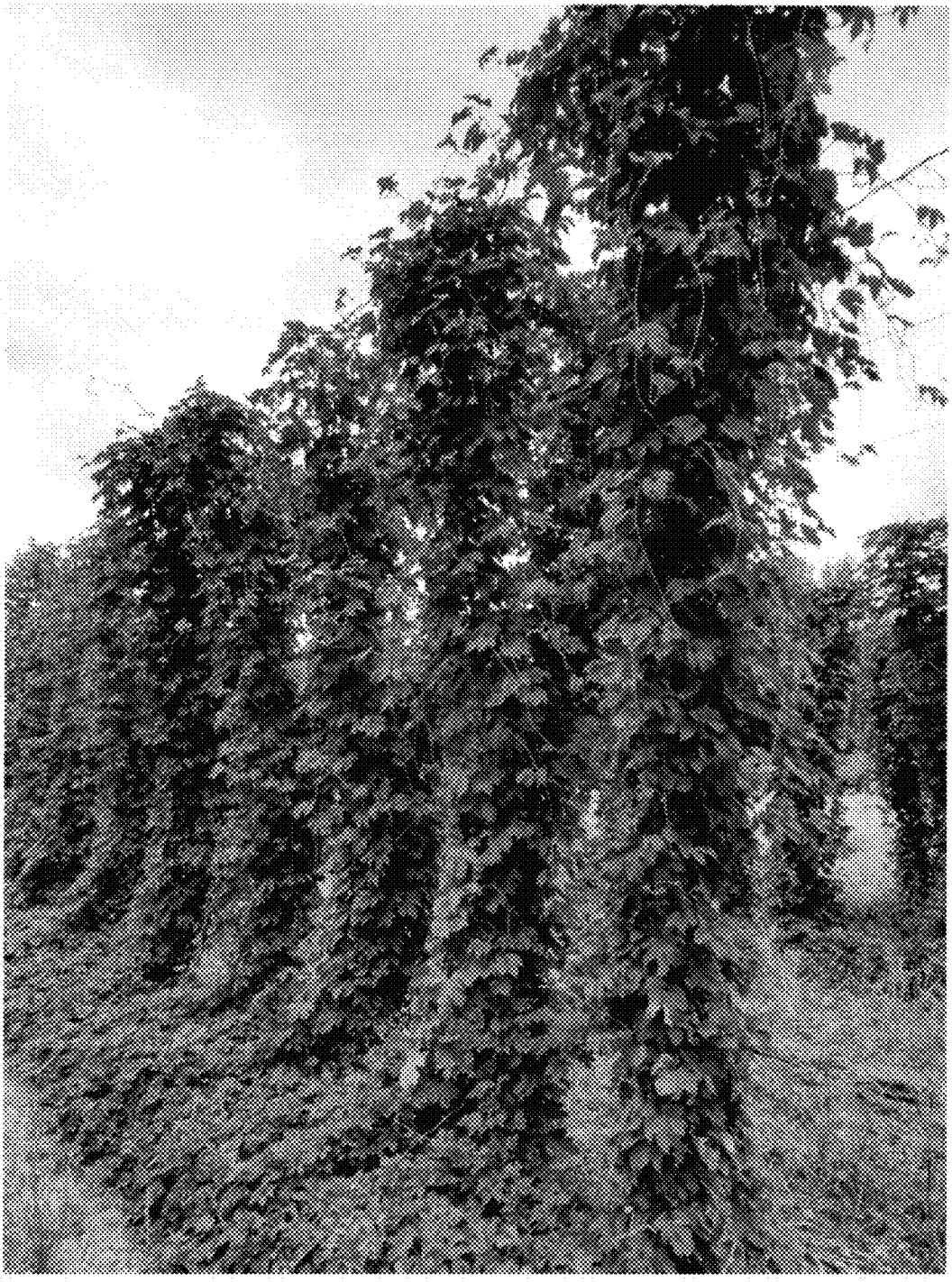
FIG. 2 shows typical three-year old 'IH13022' plants.
Figure 3:
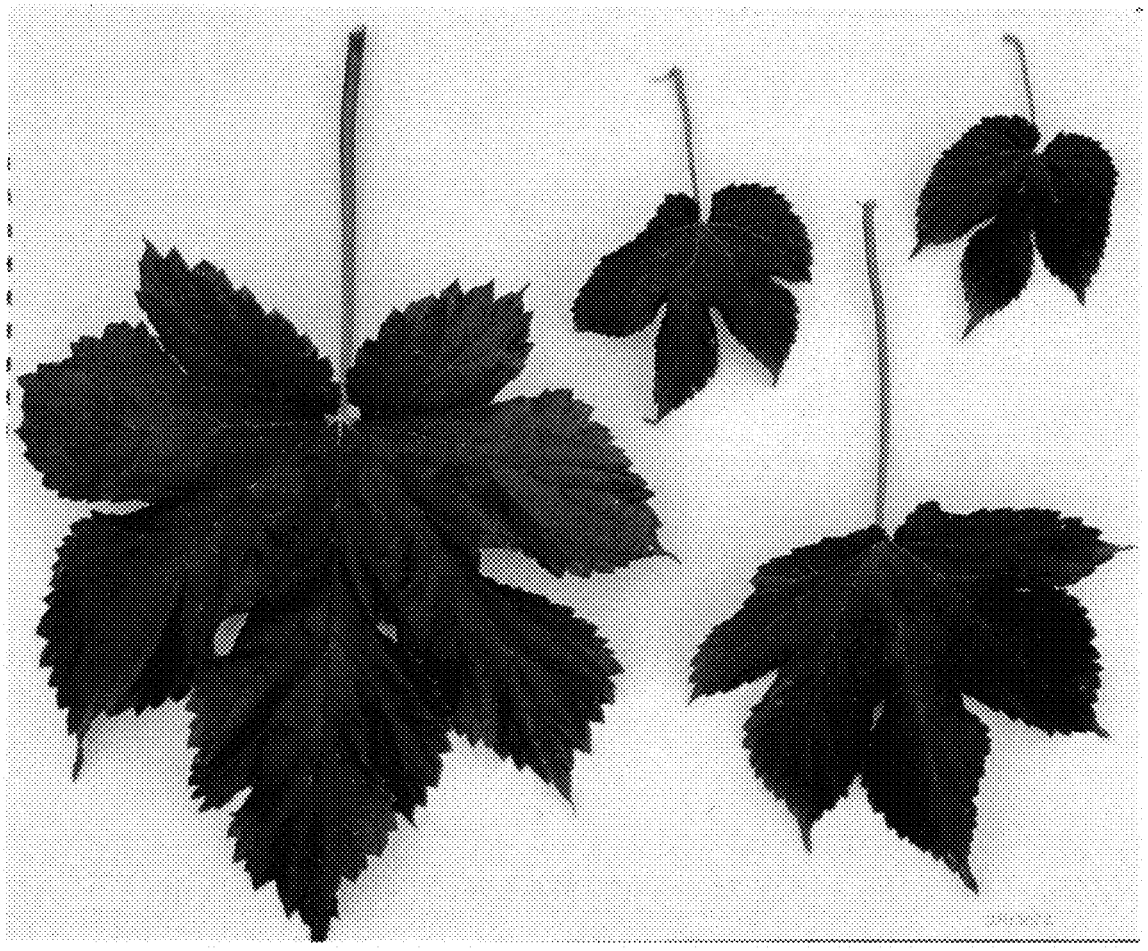
FIG. 3 shows the variable leaf lobing of 'IH13022'.
Figure 4:
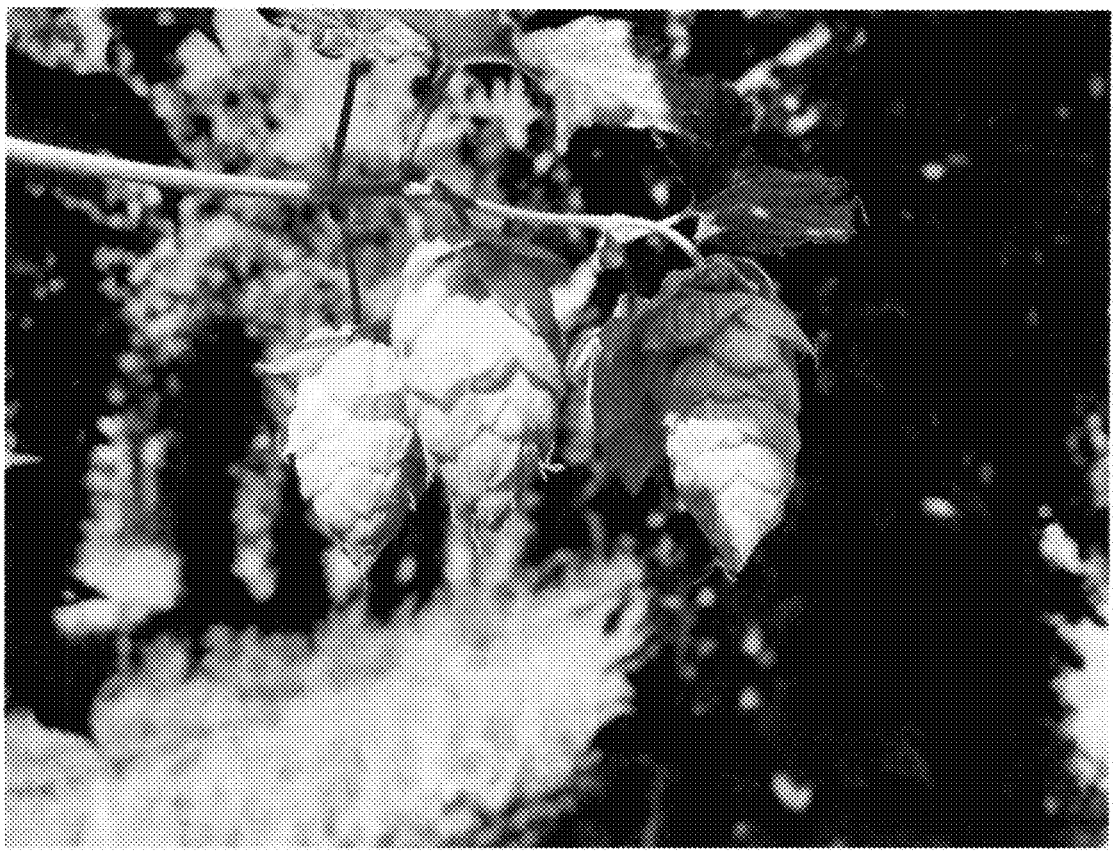
FIG. 4 shows the typical mature cones of 'IH13022'.

The following detailed description of the 'IH13022' cultivar is based on observations of various 2-4-year-old plants, $1^{st}$ propagation generation, growing on a hop farm in Oregon's Willamette Valley between 2019 and 2021. The original motherplant has been observed growing in a cultivated area near Corvallis, Oregon. The new cultivar has not been evaluated under all possible environmental conditions but was developed for Oregon's Willamette Valley (USDA hardiness zone 8b near 45 degrees North latitude). Certain characteristics of this cultivar such as growth, color, and cone chemical composition may vary with different grower practices and changing environmental conditions (e.g., light, temperature, moisture, nutrient availability, or other factors). The color descriptions are all based on The *Royal Horticultural Society* (*R.H.S.*) *Colour Chart,* $6^{th}$ edition, 2015.

Parentage:

*Female parent.*—*Humulus lupulus* 'Sorachi Ace'.
*Male parent.*—Unknown.

Comparison to Other Commercially Available Varieties

Tables 1-6 below provide comparisons between various traits of the cultivar 'IH13022', its female parent 'Sorachi Ace', and the commercially available aroma cultivar 'OR91331' (U.S. Plant Pat. No. 31,042). The aroma hop cultivar 'OR91331' was bred for the same target environment as 'IH13022', and represents a widely grown aroma hop cultivar in the target environment. 'Sorachi Ace' was developed in Japan and has very limited acreage and commercial acceptance in the United States. The cultivar 'OR91331' is ideal for aromatic, hop-forward beer styles such as an IPA (India Pale Ale).

As shown in Table 1, 'IH13022' typically yields less than 'OR91331', but similar to 'Sorachi Ace' when grown in Oregon's Willamette Valley, and the observed yield is acceptable for this region.

TABLE 1

Per-plant yield for 'IH13022' compared to 'Sorachi Ace' and 'OR91331' grown in Oregon's Willamette Valley.

| Cultivar | Yield (lbs)† | Range (lbs) |
|---|---|---|
| 'OR91331' | 9.48 a | 6.95-17.30 |
| 'IH13022' | 7.81 ab | 4.08-14.65 |
| 'Sorachi Ace' | 5.18 b | 4.52-6.20 |

†Means followed by the same letter are not statistically significant at P = 0.05.

The 'IH13022' cultivar has less alpha acids concentration than 'OR91331' but is similar to 'Sorachi Ace', and contains less beta acids than either control cultivar (Table 2). The bittering acids provide bitterness to beer during the brewing process. The cultivar 'IH13022' also contains higher amounts of cohumulone than 'OR91331', and higher colupulone than the other two cultivars. Cohumulone is the major component of the alpha acids while colupulone is the major component of the beta acids. Total essential oil content is lower than either 'Sorachi Ace' or 'OR91331'.

TABLE 2

Bittering acids and total oil content in hops of the indicated cultivars grown in Oregon's Willamette Valley.

| Cultivar | | Range |
|---|---|---|
| | Alpha Acids (%) | |
| 'OR91331' | 12.57 a | 11.58-13.52 |
| 'IH13022' | 9.56 b | 8.58-10.47 |
| 'Sorachi Ace' | 8.99 b | 8.42-9.57 |
| | Beta Acids (%) | |
| 'OR91331' | 5.28 a | 4.75-5.57 |
| 'Sorachi Ace' | 4.41 b | 4.32-4.46 |
| 'IH13022' | 3.60 c | 3.32-3.99 |
| | Total Oil (ml/100 g) | |
| 'OR91331' | 2.36 a | 1.94-3.00 |
| 'Sorachi Ace' | 2.27 a | 1.30-2.80 |
| 'IH13022' | 1.66 b | 0.83-1.92 |
| | Hop Storage Index | |
| 'IH13022' | 0.27 a | 0.25-0.28 |
| 'Sorachi Ace' | 0.23 b | 0.21-0.24 |
| 'OR91331' | 0.23 b | 0.19-0.25 |
| | Cohumulone (%) | |
| 'IH13022' | 0.28 a | 0.26-0.39 |
| 'Sorachi Ace' | 0.27 a | 0.26-0.28 |
| 'OR91331' | 0.22 b | 0.19-0.24 |
| | Colupulone (%) | |
| 'Sorachi Ace' | 0.55 a | 0.52-0.59 |
| 'IH13022' | 0.48 b | 0.46-0.51 |
| 'OR91331' | 0.43 c | 0.35-0.52 |

†Means within a chemical compound followed by the same letter are not statistically significant at P = 0.05.

Table 3 shows the concentrations of 22 essential oil components implicated in beer flavor and aroma of the indicated cultivars when grown in Oregon's Willamette Valley.

TABLE 3

Essential oil component mean concentrations and ranges (in parentheses) for 'IH13022', its female parent 'Sorachi Ace', and 'IH91331' when grown in Oregon's Willamette Valley. Data are mg/100 g dried tissue.

| Component† | 'IH13022' | 'Sorachi Ace' | 'OR91331' |
|---|---|---|---|
| a-Pinene | 2.15 a (0.84-2.64) | 1.20 a (0.15-2.51) | 2.34 a (1.39-3.19) |
| b- Pinene | 23.17 a (12.85-27.60) | 12.60 b (1.41-29.27) | 29.68 a (18.47-41.42) |
| Myrcene | 1336.53 a (743.04-1673.73) | 723.52 b (98.12-1552.22) | 1698.97 a (1080.16-2380.36) |
| Limonene | 11.58 a (6.06-17.13) | 5.69 b (0.43-14.47) | 14.89 a (9.86-20.00) |

TABLE 3-continued

Essential oil component mean concentrations and ranges (in parentheses) for 'IH13022', its female parent 'Sorachi Ace', and 'IH91331' when grown in Oregon's Willamette Valley. Data are mg/100 g dried tissue.

| Component† | 'IH13022' | 'Sorachi Ace' | 'OR91331' |
|---|---|---|---|
| Cymene | 7.11 b (4.74-8.78) | 0.02 c (0-0.05) | 13.09 a (10.55-15.97) |
| Methyl Heptanoate | 10.25 b (7.78-15.28) | 2.72 b (0-7.76) | 30.05 a (19.37-48.48) |
| Linalool | 14.17 b (11.22-17.75) | 5.43 c (0.01-12.34) | 23.20 a (15.84-31.64) |
| b-Caryophyllene | 211.07 b (71.04-274.74) | 111.61 c (1.80-218.52) | 350.37 a (296.44-446.81) |
| Terpin-4-ol | 0.59 a (0.45-0.70) | 0.04 c (0-0.09) | 0.43 b (0.19-0.77) |
| Farnesene | 20.53 ab (0-105.71) | 62.32 a (0.20-121.91) | 0.34 b (0-0.81) |
| Humulene | 316.35 b (163.84-443.73) | 333.72 b (34.89-608.25) | 730.81 a (617.10-905.64) |
| Citral 1 | 0.32 b (0.16-0.59) | 4.02 a (0-11.37 | 0.79 b (0.33-1.71) |
| Citral 2 | 1.00 a (0.73-1.89) | 2.09 a (0.01-5.00) | 0.88 a (0.44-1.68) |
| a-Terpineol | 2.71 a (0.25-4.63) | 0.09 b (0-0.16) | 1.97 ab (0.07-3.36) |
| Geranyl Acetate | 8.74 a (2.18-23.06) | 0.97 a (0-2.47) | 4.28 a (3.05-5.55) |
| Nerol | 2.98 b (2.03-4.05) | 1.03 c (0.04-2.83) | 5.89 a (4.80-8.07) |
| Geraniol | 4.09 b (2.76-5.55) | 11.78 a (1.41-20.08) | 4.07 b (1.65-8.28) |
| Caryophyllene Oxide | 1.23 a (0.26-1.72) | 2.06 a (0.29-4.79) | 1.88 a (1.67-2.12) |
| Epoxide 2 | 3.83 a (2.38-4.95) | 1.54 a (0.51-2.56) | 5.05 a (1.36-11.84) |
| 3-carene | 6.33 b (3.61-9.49) | 0.96 c (0-2.31) | 14.11 a (10.92-18.21) |
| Methyl Geranate | 5.25 b (2.34-6.60) | 0.29 b (0-0.58) | 10.55 a (0.98-16.52) |
| Geranyl Isobutyrate | 15.70 a (6.74-28.24) | 1.67 b (0.07-3.27) | 50.49 a (1.37-124.43) |

†Means within a chemical compound followed by the same letter are not statistically significant at P = 0.05.

Summary of Morphological Traits

Tables 4-7 summarize the principal morphological characteristics of 'IH13022' when grown in Oregon's Willamette Valley, as compared to female parent 'Sorachi Ace' and the industry-standard aroma hop cultivar 'OR91331', which was selected for the same growing region.

Lower Canopy Cone Measurements

Cones found in the lower canopy of 'IH13022' (Table 4):

1. have a greater number of bracts and bracteoles per cone than 'OR91331' and 'Sorachi Ace'
2. have wider cone bracts and bracteoles than 'OR91331' and 'Sorachi Ace'
3. have longer bracts than 'IH91331' and bracteoles that are longer than 'IH91331' but shorter than 'Sorachi Ace'
4. are longer and have a longer rachis (central strig) than 'IH91331' and 'Sorachi Ace'

TABLE 4

Lower canopy cone measurements for 'IH13022', the female parent 'Sorachi Ace', and 'OR91331' when grown in Oregon's Willamette Valley.

| Cultivar | Trait† | Range |
|---|---|---|
| | Number of Bracts | |
| 'IH13022' | 27.5 a | 23-32 |
| 'Sorachi Ace' | 23.9 b | 13-27 |
| 'OR91331' | 23.5 b | 22-28 |
| | Number of Bracteoles | |
| 'IH13022' | 56.3 a | 42-79 |
| 'OR91331' | 38.8 b | 31-47 |
| 'Sorachi Ace' | 31.8 b | 16-43 |
| | Cone Bract Width (cm) | |
| 'IH13022' | 1.3 a | 0.7-2.2 |
| 'Sorachi Ace' | 1.2 b | 0.7-2.2 |
| 'OR91331' | 1.1 c | 0.5-1.8 |
| | Cone Bract Length (cm) | |
| 'IH13022' | 1.9 a | 1.1-2.6 |
| 'Sorachi Ace' | 1.9 a | 1-2.8 |
| 'OR91331' | 1.7 b | 0.8-2.1 |
| | Cone Bracteole Width (cm) | |
| 'IH13022' | 0.97 a | 0.5-1.7 |
| 'Sorachi Ace' | 0.90 b | 0.6-1.1 |
| 'OR91331' | 0.90 b | 0.5-1.8 |
| | Cone Bracteole Length (cm) | |
| 'Sorachi Ace' | 1.7 a | 1.3-2.5 |
| 'IH13022' | 1.6 b | 0.8-2.3 |
| 'OR91331' | 1.5 c | 0.5-1.8 |
| | Cone Length (cm) | |
| 'IH13022' | 5.1 a | 4.4-5.9 |
| 'Sorachi Ace' | 4.3 b | 3.1-5.2 |
| 'OR91331' | 4.0 b | 3.1-4.5 |
| | Rachis Length (cm) | |
| 'IH13022' | 4.1 a | 3.6-4.9 |
| 'Sorachi Ace' | 3.3 b | 2.3-4.3 |
| 'OR91331' | 3.1 b | 2.6-4.0 |

†Means within a trait followed by the same letter are not statistically significant at P = 0.05.

Middle Canopy Cone Measurements

Cones found in the middle canopy of 'IH13022' (Table 5):

1. have a greater number of bracts and bracteoles per cone than 'OR91331' and 'Sorachi Ace'
2. have wider cone bracts and bracteoles than 'OR91331' and 'Sorachi Ace'
3. have a longer bract than 'OR91331' and longer bracteoles than 'IH91331' and 'Sorachi Ace'
4. are longer than 'OR91331' and 'Sorachi Ace'
5. have longer cone petioles than 'OR91331'

TABLE 5

Middle canopy cone measurements for 'IH13022', its female parent 'Sorachi Ace', and 'OR91331' when grown in Oregon's Willamette Valley.

| Cultivar | Trait† | Range |
|---|---|---|
| | Number of Bracts | |
| 'IH13022' | 32.8 a | 29-42 |
| 'OR91331' | 27.3 b | 22-34 |
| 'Sorachi Ace' | 21.7 c | 16-29 |

TABLE 5-continued

Middle canopy cone measurements for 'IH13022', its female parent 'Sorachi Ace', and 'OR91331' when grown in Oregon's Willamette Valley.

| Cultivar | Trait† | Range |
|---|---|---|
| | Number of Bracteoles | |
| 'IH13022' | 58.4 a | 50-67 |
| 'OR91331' | 47.8 b | 36-68 |
| 'Sorachi Ace' | 36.2 c | 22-46 |
| | Cone Bract Width (cm) | |
| 'IH13022' | 1.4 a | 0.7-2.1 |
| 'Sorachi Ace' | 1.2 b | 0.9-1.5 |
| 'OR91331' | 1.0 c | 0.3-1.7 |
| | Cone Bract Length (cm) | |
| 'IH13022' | 2.0 a | 1.2-2.9 |
| 'Sorachi Ace' | 2.0 a | 1.2-2.4 |
| 'OR91331' | 1.6 b | 0.8-2.1 |
| | Cone Bracteole Width (cm) | |
| 'Sorachi Ace' | 1.0 a | 0.7-1.9 |
| 'IH13022' | 0.9 b | 0.4-1.7 |
| 'OR91331' | 0.8 c | 0.5-1.2 |
| | Cone Bracteole Length (cm) | |
| 'Sorachi Ace' | 1.7 a | 1.3-2.0 |
| 'IH13022' | 1.6 b | 0.8-2.3 |
| 'OR91331' | 1.6 b | 0.7-2.0 |
| | Cone Length (cm) | |
| 'IH13022' | 5.4 a | 4.8-5.8 |
| 'Sorachi Ace' | 4.7 b | 3.7-5.4 |
| 'OR91331' | 4.5 b | 3.5-5.6 |
| | Rachis Length (cm) | |
| 'IH13022' | 4.1 a | 3.1-5.1 |
| 'Sorachi Ace' | 3.7 a | 2.8-4.7 |
| 'OR91331' | 3.4 a | 3.0-4.2 |

†Means within a trait followed by the same letter are not statistically significant at P = 0.05.

Morphological Characteristics

Compared to 'IH91331' when grown in Oregon's Willamette Valley, 'IH13022' (Table 6):

1. has a longer main bine internode length
2. has a longer sidearm 1st internode length
3. has a wider sidearm 1st internode diameter
4. has longer leaves
5. has a longer cone petiole

TABLE 6

Plant morphological measurements for 'IH13022' and an industry-standard aroma hop cultivar 'OR91331' when grown in Oregon's Willamette Valley.

| Cultivar | Trait (cm)† | Range (cm) |
|---|---|---|
| | Main Bine Internode Length | |
| 'IH13022' | 32.4 a | 26.8-36.7 |
| 'OR91331' | 20.5 b | 11.4-29.2 |
| | Main Bine Diameter | |
| 'IH13022' | 0.8 a | 0.6-1.0 |
| 'OR91331' | 0.7 a | 0.6-0.8 |
| | Sidearm Length | |
| 'IH13022' | 91.9 a | 58.1-130.4 |
| 'OR91331' | 73.5 a | 45.6-103.5 |

TABLE 6-continued

Plant morphological measurements for 'IH13022' and an industry-standard aroma hop cultivar 'OR91331' when grown in Oregon's Willamette Valley.

| Cultivar | Trait (cm)† | Range (cm) |
|---|---|---|
| | Sidearm 1st Internode Length | |
| 'IH13022' | 26.0 a | 18.5-32.9 |
| 'OR91331' | 20.0 b | 13.5-29.9 |
| | Sidearm 1st Internode Diameter | |
| 'IH13022' | 0.43 a | 0.4-0.5 |
| 'OR91331' | 0.31 b | 0.3-0.4 |
| | Leaf Length | |
| 'IH13022' | 17.9 a | 10.1-21.4 |
| 'OR91331' | 12.2 b | 7.9-19.3 |
| | Leaf Width | |
| 'IH13022' | 20.1 a | 10.6-28.8 |
| 'OR91331' | 13.9 a | 7.6-23.8 |
| | Leaf Petiole Length | |
| 'IH13022' | 11.63 a | 6.5-16.4 |
| 'OR91331' | 11.13 a | 4.9-16.6 |
| | Leaf Petiole Diameter | |
| 'IH13022' | 0.43 a | 0.2-0.6 |
| 'OR91331' | 0.39 a | 0.2-0.7 |
| | Cone Petiole Length | |
| 'IH13022' | 5.7 a | 2.7-9.3 |
| 'OR91331' | 3.9 b | 2.5-5.4 |
| | Cone Petiole Diameter | |
| 'IH13022' | 0.1 a | 0.1 |
| 'OR91331' | 0.1 a | 0.1 |

†Means within a trait followed by the same letter are not statistically significant at P = 0.05.

Table 7 lists additional plant characteristics for 'IH 13022'.

TABLE 7

Qualitative mid-canopy data collected from hop cultivar 'IH13022' when grown in Oregon's Willamette Valley.

| Trait | Description |
|---|---|
| Ploidy | 2X (diploid) |
| Plant | Vigorous climbing bine |
| Shape | Columnar |
| Plant head volume | Medium |
| Foliage density | Medium |
| Target area | Oregon's Willamette Valley (USDA hardiness zone 8b near latitude 45 degree North) |
| Bine | |
| Shape | Hexagonal |
| Color | 144D |
| Striping | 183B |
| Total length (ft) | 21+ |
| Leaf Petiole | |
| Color | NN143A with NN183B |
| Shape | Flat upper surface with channel |
| Leaf | |
| Arrangement | Opposite |
| Shape | Immature = 3-lobed, Mature = mix of 3- to 9-lobed |
| Color | Upper = 137A, lower = NN147B |
| Venation | primary order: palmate<br>secondary order: craspedodromous |

TABLE 7-continued

Qualitative mid-canopy data collected from hop cultivar 'IH13022' when grown in Oregon's Willamette Valley.

| Trait | Description |
|---|---|
| Vein color | NN144B |
| Blistering | Absent |
| Leaf margin | Serrated |
| Ligule color | 144C |
| Adaxial leaf texture | pubescent |
| Abaxial leaf texture | pubescent |
| Cone | |
| Shape | Ovate |
| Degree of opening | Petiole end: open<br>Rest of cone: closed |
| Flowering date | July 16-24 |
| Maturity date | September 2-5 |
| Cone distribution | Evenly distributed throughout plant |
| Petiole color | 144A |
| Bract color | 149D |
| Bracteole color | 145C |
| Rachis color | 138D |

Sensory Observations

Internal sensory evaluations of hop cones from 'IH13022' took place from October 2019 through November 2020. These evaluations include "dry rub" analysis via human sensory for aromatic character, as well as "dry hop" analysis again for human analysis of how the hop character expresses in beer. The "dry rub" involves rubbing the dried hop cones aggressively between a person's hands to rupture the lupulin glands and volatize the oils, at which point experienced personnel evaluate and record the aromatics. "Dry hop" analysis involves adding the dried hop cone material into a neutral base beer and allowing time for the hop oils to transfer into the beer so that hop flavor and aroma can be evaluated in the finished product. The primary sensory observations collected from test brews can be summarized as "bright, fresh peach-lemonade, candied orange peel, mango, boysenberry and guava."

Another unique characteristic of the hop cones from 'IH13022' is that they are void of the typical resinous character (aroma/flavor reminiscent of coniferous tree sap/pitch) that normally comes along with such hops of above average intensity.

I claim:

1. A new and distinct variety of hop plant named 'IH13022', substantially as illustrated and described herein.

* * * * *